United States Patent
Takahashi et al.

(10) Patent No.: US 12,429,420 B2
(45) Date of Patent: Sep. 30, 2025

(54) GAS ANALYSIS APPARATUS AND GAS ANALYSIS METHOD

(71) Applicant: HORIBA STEC, Co., Ltd., Kyoto (JP)

(72) Inventors: Motonobu Takahashi, Kyoto (JP); Sotaro Kishida, Kyoto (JP); Akira Kuwahara, Kyoto (JP); Takeshi Akamatsu, Kyoto (JP); Yuhei Sakaguchi, Kyoto (JP); Masakazu Minami, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 264 days.

(21) Appl. No.: 18/095,204

(22) Filed: Jan. 10, 2023

(65) Prior Publication Data

US 2023/0228677 A1 Jul. 20, 2023

(30) Foreign Application Priority Data

Jan. 19, 2022 (JP) .................. 2022-006561

(51) Int. Cl.
*G01N 21/3504* (2014.01)
*G01D 11/24* (2006.01)
*G01D 21/02* (2006.01)
*G01N 33/00* (2006.01)

(52) U.S. Cl.
CPC ....... *G01N 21/3504* (2013.01); *G01D 11/245* (2013.01); *G01D 21/02* (2013.01); *G01N 33/0027* (2013.01)

(58) Field of Classification Search
CPC .......... G01N 21/3504; G01N 33/0027; G01N 2201/1218; G01N 21/0332; G01N 33/0016; G01N 21/01; G01N 2021/3536; G01D 11/245; G01D 21/02; G01L 9/125; G01L 9/0072; G01L 19/14
See application file for complete search history.

(56) References Cited

U.S. PATENT DOCUMENTS

| | | | |
|---|---|---|---|
| 6,324,897 B1* | 12/2001 | Schrenk | G01N 21/783 73/31.05 |
| 9,835,556 B2* | 12/2017 | Ido | G01N 21/3504 |
| 2007/0182965 A1* | 8/2007 | Kamlet | G01N 21/05 356/437 |
| 2008/0225296 A1* | 9/2008 | Liu | G01N 21/3504 356/437 |
| 2011/0090505 A1* | 4/2011 | Kuze | G01N 21/3504 977/954 |
| 2011/0290031 A1* | 12/2011 | Kuwahara | G01L 19/0627 73/724 |
| 2012/0197554 A1* | 8/2012 | Glaudel | G01L 9/0072 73/718 |
| 2017/0082537 A1* | 3/2017 | Ido | G01N 21/3504 |
| 2018/0283971 A1* | 10/2018 | Kishida | G01L 19/147 |

FOREIGN PATENT DOCUMENTS

JP 2012-230011 A 11/2012

* cited by examiner

*Primary Examiner* — Jonathan M Hansen
(74) *Attorney, Agent, or Firm* — Greenblum & Bernstein, P.L.C.

(57) ABSTRACT

Provided are a gas cell into which a gas is introduced, a temperature control block configured to control a temperature of the gas cell, and a pressure sensor configured to measure a pressure inside the gas cell. The pressure sensor is built into the temperature control block and/or the gas cell.

8 Claims, 8 Drawing Sheets

GAS ANALYSIS APPARATUS AND GAS ANALYSIS METHOD

BACKGROUND

Technical Field

The present invention relates to a gas analysis apparatus and a gas analysis method.

Related Art

In a gas analysis apparatus that uses infrared absorption spectroscopy to measure a component of a gas, pressure inside a gas cell is used to measure the concentration of the component accurately, as disclosed in JP 2012-230011 A. In order to measure the pressure inside the gas cell accurately, a method of installing a pressure sensor directly in the gas cell, not via a pipe or the like, has been developed.

In such a configuration, a capacitive pressure sensor, for example, is used, as the pressure sensor. The capacitive pressure sensor includes a diaphragm that deforms with pressure and a fixed electrode that is provided in a manner facing the diaphragm, and is configured to convert the capacitance generated between the diaphragm and the fixed electrode into pressure.

However, because the diaphragm deforms with temperature, too, in order to measure the pressure accurately, it is necessary to control the temperature of the sensor body uniformly. Therefore, a sensor temperature control mechanism is provided around the sensor body of the pressure sensor. If the pressure sensor having such a sensor temperature control mechanism is mounted on the gas cell, the size of the gas analysis apparatus becomes increased.

PRIOR ART DOCUMENT

Patent Document

JP 2012-230011 A

SUMMARY

Therefore, the present invention has been made in consideration of the problem described above, and a main object of the present invention is to reduce the size of a gas analysis apparatus, while controlling the temperature of the pressure sensor.

In other words, a gas analysis apparatus according to the present invention is characterized by including a gas cell into which a gas is introduced; a temperature control block configured to control a temperature of the gas cell; and a pressure sensor configured to measure a pressure inside the gas cell, and in that the pressure sensor is built into the temperature control block and/or the gas cell.

In such a gas analysis apparatus, because the pressure sensor is built into the temperature control block and/or the gas cell, the temperature of the pressure sensor can be controlled using the temperature control block. As a result, it is not necessary to provide a separate temperature control mechanism for controlling the temperature of the pressure sensor, and to reduce the size of the gas analysis apparatus. In addition, by controlling the temperature of the pressure sensor, the accuracy of the pressure measurement can be improved, and the concentration of a gas component can be measured highly accurately. Furthermore, by installing the pressure sensor in a manner built into the gas cell, the distance between the optical path (concentration measurement point) and a pressure detection position, the pressure being to be used for correction, is reduced as much as possible, and a deviation in their response time is also reduced. Therefore, the accuracy of concentration reading can be improved.

In order to accurately calculate the concentration of a gas component, it is necessary to measure the pressure accurately even when the pressure inside the gas cell is low (e.g., 10 Torr (about 1333 Pa) or below, or even 1 Torr (about 133 Pa) or below). For this purpose, it is preferable for the pressure sensor to be a capacitive pressure sensor.

It is preferable for the pressure sensor to include a sensor body that includes a pressure-sensitive element, and for the sensor body to be fixed to the gas cell by a flange member and to have its temperature controlled by the temperature control block via the flange member.

With this configuration, because the temperature of the sensor body is controlled indirectly via the flange member, a temperature change caused by the effect of disturbance propagates slowly. Therefore, it is possible to make the sensor body less susceptible to the effect of disturbance. In addition, it is possible to suppress a thermal distribution across the sensor body. As a result, a pressure can be measured accurately.

It is preferable that a gap to be provided between an outer peripheral surface of the sensor body and the flange member.

By providing the gap in the manner described above, it is possible to control the temperature of the sensor body while suppressing thermal distribution across the sensor body, and to measure the pressure accurately.

It is preferable to further include a cover portion that covers a rear end surface of the sensor body with a gap therebetween, the rear surface being on a side opposite to a sensor surface of the sensor body.

By providing a gap not only on the outer peripheral surface of the sensor body but also on the rear end surface of the sensor body, it is possible to control the temperature of the sensor body while further preventing the thermal distribution across the sensor body, and to measure the pressure accurately.

As a specific embodiment for fixing the sensor body to the gas cell, it is preferable for a collar to be provided on an outer peripheral surface of the sensor body, and for the flange member to include an attaching portion that is to be attached to the gas cell, and a support that extends from the attaching portion and that is connected to the collar of the sensor body.

It is preferable for the pressure sensor to include a circuit board configured to process a detection signal, and that the circuit board is provided outside the temperature control block via a signal cable.

With this configuration, because the circuit board can be kept away from the heat source (in this example, the temperature control block), it is possible to suppress thermal effect on the circuit board.

It is preferable for the temperature control block to include a plurality of heaters, and for temperatures of the plurality of heaters to be controlled individually.

With this configuration, it is possible to control the temperature appropriately, by dividing the areas of the temperature control block into temperature control areas for the pressure sensor and for the gas cell, for example.

A gas analysis method according to the present invention is characterized by using a gas analysis apparatus including: a gas cell into which a gas is introduced; a temperature control block configured to control a temperature of the gas cell; and a pressure sensor configured to measure a pressure inside the gas cell, and in that the pressure sensor is built into the temperature control block and/or the gas cell.

According to the present invention described above, the gas analysis apparatus can be reduced in size, while controlling the temperature of the pressure sensor.

DETAILED DESCRIPTION

A gas analysis apparatus according to an embodiment of the present invention will now be explained with reference to some drawings. Note that, to facilitate understanding, all of the drawings described below are schematically illustrated, with some omissions and exaggerations made as appropriate. The same components are denoted by the same reference numerals, and the descriptions thereof will be omitted as appropriate.
<Apparatus Configuration>

The gas analysis apparatus 100 according to the present embodiment is used in a manner incorporated in a semiconductor manufacturing apparatus, and measures a concentration or a partial pressure of a target component that is contained in a material gas used in a semiconductor manufacturing process, or that is contained in a by-product gas generated in the semiconductor manufacturing process (hereinafter, these gases will be simply referred to as "gas"), for example, using infrared absorption spectroscopy.

Figure 1:
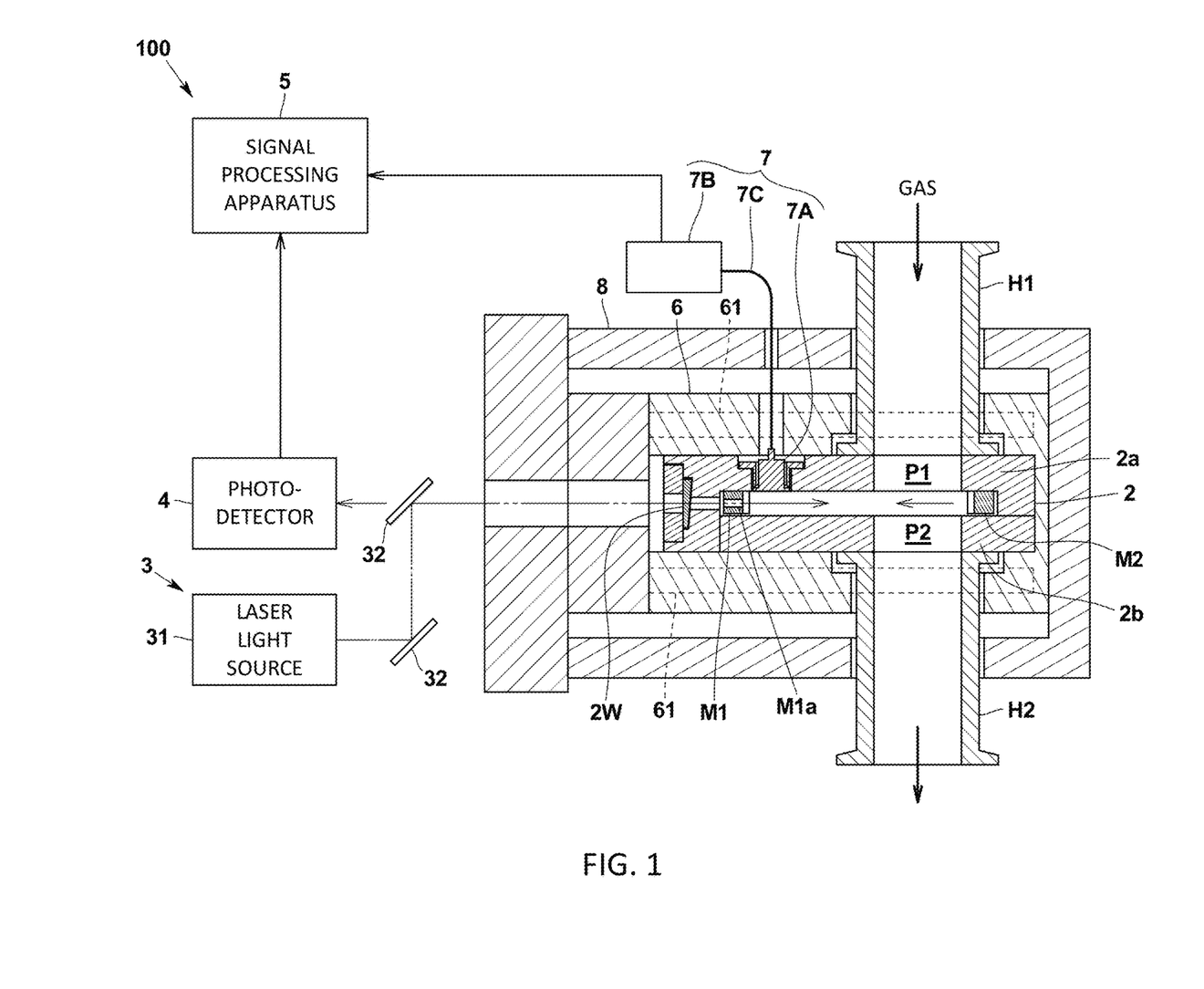
FIG. 1 is a diagram schematically illustrating a configuration of a gas analysis apparatus according to an embodiment of the present invention.

Specifically, as illustrated in FIG. 1, the gas analysis apparatus 100 includes a gas cell 2 into which a gas is introduced, a light irradiating unit 3 that emit light into the gas cell 2, a photodetector 4 that detects the light having passed through the gas cell 2, and a signal processing apparatus 5 that calculates the concentration of a component contained in the gas, using an output signal from the photodetector 4.

The gas cell 2 is a multi-reflection cell, and has an optical window 2W on which the light becomes incident and from which the light goes out, and a pair of reflection mirrors M1 and M2 is provided inside the gas cell 2. One of the reflection mirrors M1 is provided with a light transmitting portion M1a for guiding the incident light from the optical window 2W into the space between the pair of reflection mirrors M1 and M2, and for guiding the light having multiple-reflected by the pair of reflection mirrors M1 and M2 to the photodetector 4, via the optical window 2W.

The gas cell 2 is made of a corrosion-resistant material such as stainless steel e.g., SUS316L. The optical window 2W is made of a transparent material, such as quartz, calcium fluoride, barium fluoride, sapphire, or zinc selenide that absorbs almost no light within the absorption range of the wavelength of the target component.

In a pair of facing walls 2a and 2b that form the gas cell 2, a gas inlet port P1 is provided to the facing wall 2a, and an upstream pipe H1 is connected to the gas inlet port P1. A pair of reflection mirrors M1 and M2 is also fixed to the facing wall 2a. A gas outlet port P2 is provided on the other facing wall 2b, and a downstream pipe H2 is connected to the gas outlet port P2.

A temperature control block 6 for controlling the temperature inside the gas cell 2 is provided around the gas cell 2. The gas cell 2 is provided with a pressure sensor 7 that measures the pressure inside the gas cell 2. The temperature control block 6 and the pressure sensor 7 will be explained later in <Pressure sensor 7 and structures therearound>.

The light irradiating unit 3 according to the present embodiment includes a laser light source 31 and an optical system 32, such as a reflection mirror, that guides the laser light from the laser light source 31 into the gas cell 2.

The laser light source 31 according to the present embodiment is a semiconductor laser. Specifically, the laser light source 31 is a quantum cascade laser (QCL) that is a type of semiconductor laser, and oscillates a laser beam in a mid-infrared range (2.5 μm to 25 μm). The laser light source 31 is enabled to modulate (change) the oscillation wavelength by a current (or a voltage) given thereto. Note that any other types of laser may be used, as long as an oscillation wavelength can be changed. Furthermore, the oscillation wavelength may also be changed by changing the temperature or the like. The laser light source 31 is controlled by a light source control unit 51a provided by the signal processing apparatus 5.

In the present embodiment, a relatively inexpensive thermal photodetector, such as a thermopile, is used as the photodetector 4, but may also be a photodetector of any other type of photodetector, such as a quantum type photoelectric element that is highly responsive, e.g., HgCdTe, InGaAs, InAsSb, or PbSe.

Figure 2:
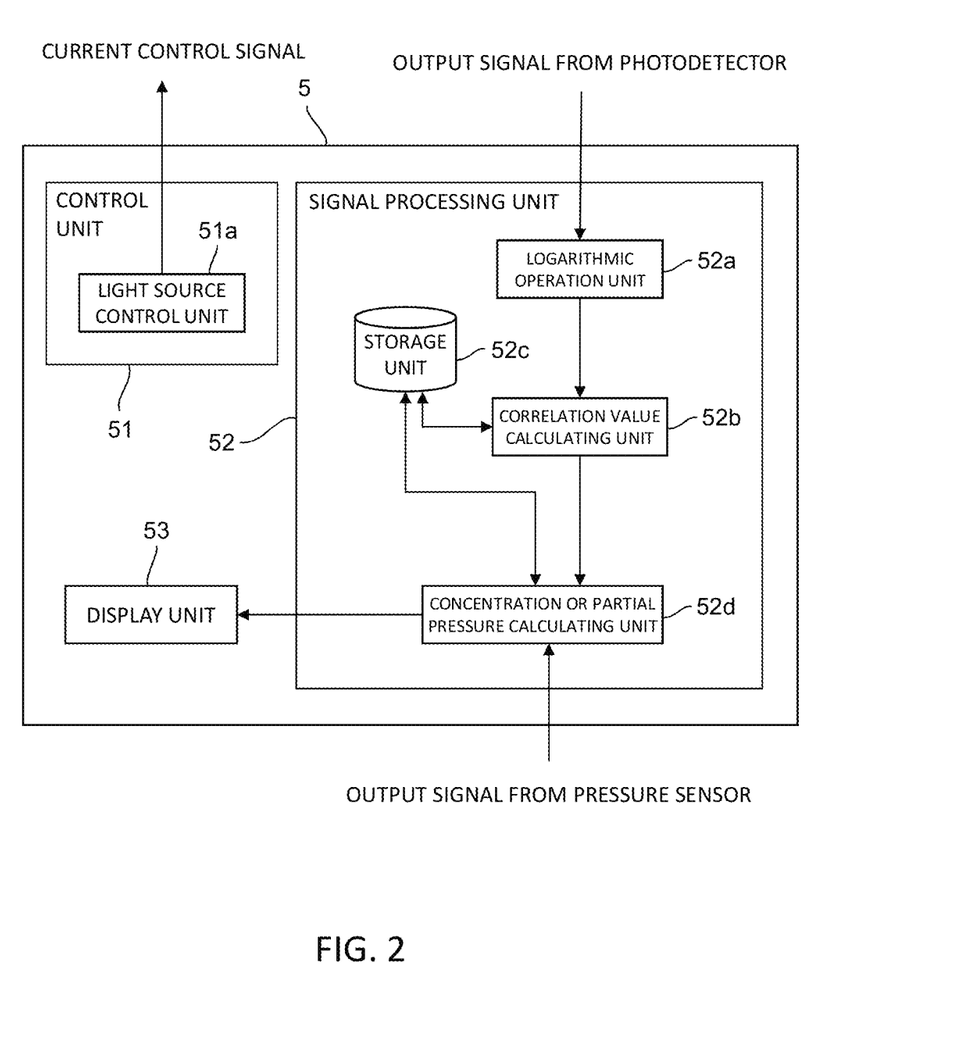
FIG. 2 is a functional block diagram of a signal processing apparatus according to the embodiment.

The signal processing apparatus 5 includes analog electric circuits that include a buffer and an amplifier, and digital electric circuits that includes a CPU and a memory, and an AD converter and a DA converter that serve as mediators between the analog/digital electric circuits. The signal processing apparatus 5 exerts functions as a control unit 51 that controls the laser light source 31 or the heater 61 described above included in gas analysis apparatus 100, and as a signal processing unit 52 that receives an output signal from the photodetector 4 and performs an arithmetic operation on the signal and calculates a concentration of or a partial pressure of a target component, by causing the CPU and peripheral devices to cooperate with one another in accordance with a predetermined computer program stored in a predetermined area of the memory, as illustrated in FIG. 2.

These units will now be explained in detail one by one.

The control unit 51 includes a light source control unit 51a that controls the output from the laser light source 31. This light source control unit 51a outputs a current (or voltage) control signal to control a current source (or a voltage source) of the laser light source 31. The control unit 51 also performs various controls such as control of the heater 61, by outputting a control signal to a temperature controller (not illustrated) to be described later, using a temperature sensor (not illustrated) provided in the gas cell 2.

Specifically, the light source control unit 51a changes a current (or a voltage) for driving the laser light source 31 at a predetermined frequency, to modulate the laser oscillation wavelength at the predetermined frequency with respect to a center frequency. As a result, the laser light source 31 is caused to emit modulated light having been modulated at the predetermined modulation frequency. In addition, the light source control unit 51a also modulates the laser oscillation wavelength across a wavelength modulation range including a feature of a light absorption signal corresponding to the target component.

Figure 3:
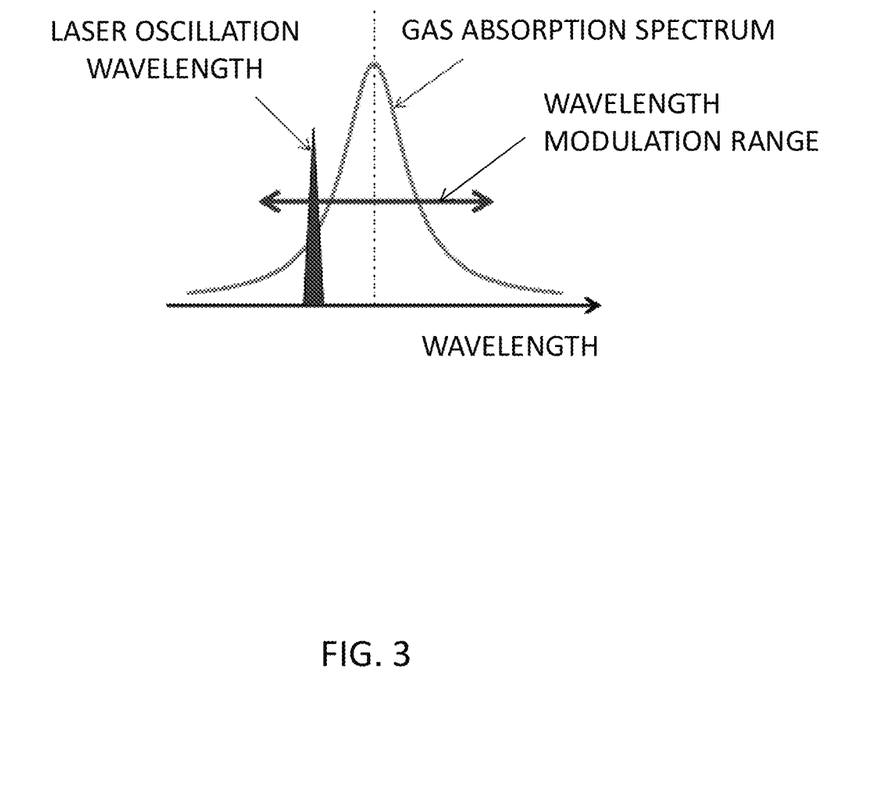
FIG. 3 is a schematic diagram illustrating a method for modulating a laser oscillation wavelength in the embodiment.
Figure 4:
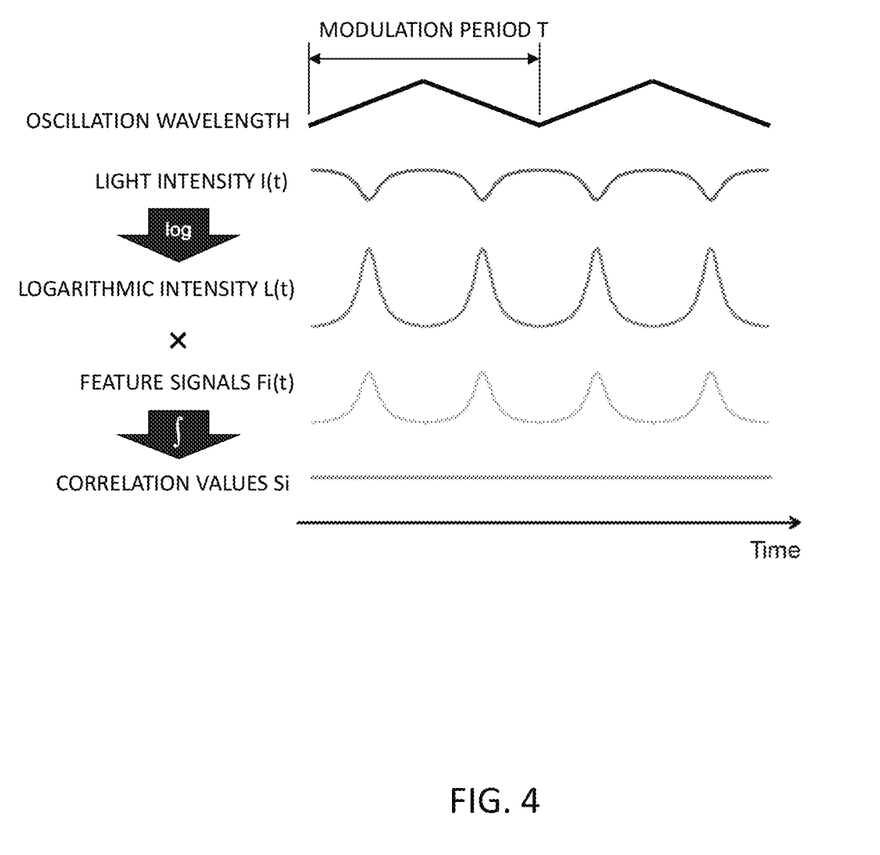
FIG. 4 is a time-series graph illustrating an example of an oscillation wavelength, a light intensity I(t), a logarithmic intensity L(t), a feature signal $F_i(t)$, and a correlation value $S_i(t)$ according to the embodiment.

In this embodiment, the light source control unit 51a changes the driving current to a triangular wave to modulate the oscillation frequency to a triangular wave (see "oscillation wavelength" in FIG. 4). In practice, the driving current is modulated by another function so that the oscillation frequency delineates a triangular waveform. As illustrated in FIG. 3, the laser oscillation wavelength is modulated so as to have a center wavelength at a peak or near the peak of an absorption spectrum of the target component. The light source control unit 51a may also change the driving current to a sinusoidal form, a saw teeth form, or an arbitrary functional form to modulate the oscillation frequency to a sinusoidal form, a saw-teeth form, or an arbitrary functional form, respectively.

The signal processing unit 52 includes a logarithmic operation unit 52a, a correlation value calculating unit 52b, a storage unit 52c, and a concentration or partial pressure calculating unit 52d.

The logarithmic operation unit 52a executes a logarithmic operation to a light intensity signal that is an output signal from the photodetector 4. A function I(t) that represents temporal changes of the light intensity signal obtained by the photodetector 4 over time is plotted as indicated as "light intensity I(t)" in FIG. 4, and a plot resultant of the logarithmic operation is as indicated as "logarithmic intensity L(t)" in FIG. 4.

The correlation value calculating unit 52b calculates a correlation value for an intensity-related signal that is related to an intensity of sample light, with respect to each of a plurality of predetermined feature signals. A feature signal is a signal for extracting a feature of the waveform of the intensity-related signal, by establishing a correlation to the intensity-related signal. As the feature signal, a sine wave signal or signals of other various types corresponding to waveform features to be extracted from the intensity-related signal.

An example using a feature signal other than a sine wave signal will now be explained. The correlation value calculating unit 52b calculates correlation values of an intensity-related signal that is related to the intensity of sample light, with respect to a plurality of respective feature signals, the feature signals being those with which correlations different from a sine wave signal (sine function) can be obtained. As the intensity-related signal, the correlation value calculating unit 52b uses a light intensity signal applied with a logarithmic operation (logarithmic intensity L(t)).

The correlation value calculating unit 52b also calculates, using the equation below (Equation 1), a plurality of sample correlation values $S_i$ that are correlation values of the intensity-related signal corresponding to the sample light with respect to respective feature signals $F_i(t)$ (i=1, 2, . . . , n) the number of which is greater than the sum of the number of the types of target components and the number of types of interference components. Note that T in the following equation (Equation 1) denotes a modulation period.

$$S_i = \int_0^T L(t) \cdot F_i(t) dt \ (i=1,2,\ldots,n)$$

$$R_i = \int_0^T L_0(t) \cdot F_i(t) dt \ (i=1,2,\ldots,n)$$

$$S_i' = S_i - R_i \qquad \text{[Equation 1]}$$

When the sample correlation values are calculated, the correlation value calculating unit 52b preferably calculates corrected sample correlation values $S_i'$. This correction is made by subtracting reference correlation values $R_i$ from the correlation values $S_i$ of the intensity-related signal L(t) of the sample light with respect to the plurality of feature signals $F_i(t)$, respectively, where the reference correlation values $R_i$ are correlation values of an intensity-related signal $L_0(t)$ corresponding to reference light with respect to the plurality of respective feature signals $F_i(t)$, as indicated in Equation (1). In this manner, offsets included in the sample correlation values can be removed to achieve correlation values that are proportional to the concentrations or partial pressures of the target component and of the interference component. Therefore, the measurement errors can be reduced. Note that a configuration not subtracting the reference correlation values is also possible.

The reference light may be obtained at the same timing as when the sample light is obtained, before or after the measurement, or any timing. The intensity-related signal or the reference correlation values corresponding to the reference light may be obtained and stored in the storage unit 52c in advance. A possible method for obtaining the reference light at the same time includes, for example, is providing two photodetectors 4, splitting the modulated light from the laser light source 31 with a beam splitter or the like, and using one for the sample light measurement and the other for the reference light measurement.

In the present embodiment, the correlation value calculating unit 52b uses a function better capable of capturing a waveform feature of the logarithmic intensity L(t), being better than that achieved with a sine function, as the plurality of feature signals $F_i(t)$. When the sample gas contains the target component and one interference component, two or more feature signals $F_1(t)$ and $F_2(t)$ may be used. As the two or more feature signals $F_1(t)$ and $F_2(t)$, a function based on a Lorentz function that is close to the form of the absorption spectrum, and a differential function that is based on the Lorentz function may be used, for example. As feature signals, a function based on the Voigt function or a function based on the Gaussian function may also be used, instead of the function based on the Lorentz function, for example By using such functions for the feature signals, it is possible to achieve higher correlation values, compared with those obtained with a sine function. Therefore, measurement accuracy can be improved.

At this time, it is preferable to control the offset so that the DC component of the feature signal is removed, that is, so that the offset resultant of integrating the feature signal over the modulation period becomes zero. In this manner, the effect resultant of the offset added to the intensity-related signal, the offset being added due to a fluctuation in the light intensity, can be removed. It is also possible to, instead of removing the DC component of the feature signal, remove the DC component of the intensity-related signal, or to remove the DC component of both of the feature signal and the intensity-related signal. Furthermore, it is also possible to use sampled values of absorption signals corresponding to the target component and/or the interference component, or simulations thereof, as the feature signals.

Note that, by using a sequence of orthogonal functions that are orthogonal to one another, or a sequence of functions close to orthogonal functions, as two feature signals $F_1(t)$ and $F_2(t)$, the features of the logarithmic intensities L(t) can be extracted more efficiently, and the accuracy of the concentration or the partial pressure calculated with simultaneous equations, which will be described later, can be improved.

The storage unit 52c stores therein single correlation values. A single correlation value is a per-unit concentration or per-unit partial pressure correlation value corresponding to each of the target component and the interference components, the single correlation value being obtained from the intensity-related signal obtained only with the presence of that target component or interference component, and from each of the plurality of feature signal $F_i(t)$. The feature signals $F_i(t)$ used in obtaining the single correlation values are the same as the plurality of feature signals $F_i(t)$ used in the correlation value calculating unit 52b.

When a single correlation is to be stored in the storage unit 52c, it is preferable to store a single correlation value resultant of subtracting the reference correlation value from the correlation value obtained only with the presence of that target component or interference component, and of applying a correction for converting the single correlation value into a per-unit concentration or per-unit partial pressure correlation value. In the manner described above, it is possible to remove the offset included in the single correlation value, and to achieve correlation value that is proportional to the concentration or the partial pressure of the target component or the interference component. Therefore, it is possible to reduce a measurement error. Note that a configuration not subtracting the reference correlation values is also possible.

The concentration or partial pressure calculating unit 52d calculates the concentration or partial pressure of the target component using the plurality of sample correlation values obtained by the correlation value calculating unit 52b.

Specifically, the concentration or partial pressure calculating unit 52d calculates the concentration or partial pressure of the target component based on the plurality of sample correlation values obtained by the correlation value calculating unit 52b and the plurality of single correlation values stored in the storage unit 52c. More specifically, the concentration or partial pressure calculating unit 52d calculates the concentration or partial pressure of the target component by solving simultaneous equations including the plurality of sample correlation values obtained by the correlation value calculating unit 52b, the plurality of single correlation values stored in the storage unit 52c, and the concentrations or partial pressures of the target component and the interference components, respectively (see FIG. 5). The signal processing unit 52 can also correct the concentration or the partial pressure of the target component obtained by the concentration or partial pressure calculating unit 52d using the total pressure obtained by the pressure sensor 7. The concentration or the partial pressure of the target component obtained by the concentration or partial pressure calculating unit 52d in the manner described above is displayed on the display unit 53, such as a display provided on the signal processing apparatus 5, or another display unit connected to the signal processing apparatus 5.

An example of an operation of the gas analysis apparatus 100 will now be explained, also to explain the units described above in details.

<Reference Measurement>

To begin with, the light source control unit 51a controls the laser light source 31 to modulate the laser oscillation wavelength within a predetermined wavelength modulation range, at the modulation frequency and with the center at the peak of the absorption spectrum of the target component or near the peak. Before carrying out the reference measurement using a span gas, the reference measurement using a zero gas may be performed to measure the reference correlation values.

A span gas (gas the component concentration or partial pressure of which is known) is introduced into the gas cell 2 by an operator or automatically, and reference measurement is carried out. The reference measurements are collected using a span gas only containing the target component, and a span gas only containing the interference component.

Specifically, in the reference measurement, the logarithmic operation unit 52a receives the output signal from the photodetector 4, and calculates logarithmic intensity L(t). The correlation value calculating unit 52b then calculates a correlation value of the logarithmic intensity L(t) with respect to the two feature signals $F_1(t)$ and $F_2(t)$, respectively, and calculates single correlation values that are correlation values per unit concentration or per-unit partial pressures of the respective span gases, by subtracting the reference correlation values from the correlation values, and dividing the resultant values by the concentration or partial pressures of the respective span gases. Instead of calculating the single correlation values, a relationship between the concentration or the partial pressure of each of the span gases, and the correlation value corresponding to the span gas may be stored.

Specifically, this is done in the manner described below.

Figure 5:
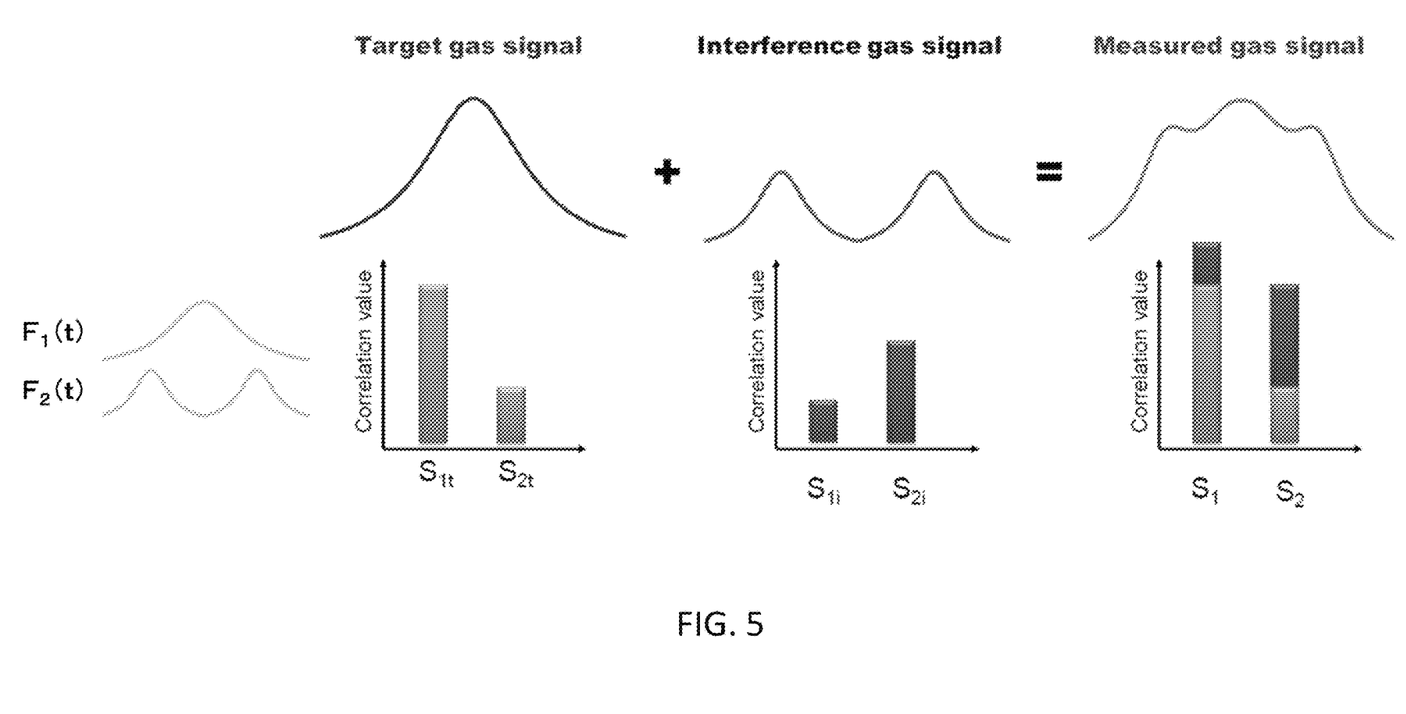
FIG. 5 is a conceptual diagram of a concentration or partial pressure calculation using single correlation values and sample correlation values according to the embodiment.

By introducing a span gas containing only the target component is into the gas cell 2, the correlation value calculating unit 52b calculates correlation values $S_{1t}$, $S_{2t}$ for the target component (see FIG. 5). At this time, $S_{1t}$ is a correlation value with a first feature signal, and $S_{2t}$ is a correlation value with a second feature signal. The correlation value calculating unit 52b then calculates the single correlation values $s_{1t}$ and $s_{2t}$ by subtracting the reference correlation values $R_i$ from the correlation values $S_{1t}$ and $S_{2t}$, respectively, and dividing the respective differences by the span gas concentration or the partial pressure $c_t$ of the target component. Note that the span gas concentration or the partial pressure $c_t$ of the target component is input to the signal processing unit 52 by a user or the like in advance.

In addition, by introducing a span gas containing only the interference component into the gas cell 2, the correlation value calculating unit 52b calculates correlation values $S_{1i}$ and $S_{2i}$ for the interference component (see FIG. 5). At this time, $S_{1i}$ is a correlation value with the first feature signal, and $S_{2i}$ is a correlation value with the second feature signal. The correlation value calculating unit 52b then calculates the single correlation values $s_{1i}$ and $s_{2i}$ by subtracting the reference correlation values $R_i$ from the correlation values $S_{1i}$ and $S_{2i}$, respectively, and dividing the respective differences by the span gas concentration or the partial pressure $c_i$ of the interference component. The span gas concentration or partial pressure $c_i$ of the interference component is input to the signal processing unit 52 by a user or the like in advance.

The single correlation values $s_{1t}$, $s_{2t}$, $s_{1i}$, and $s_{2i}$ calculated as described above are stored in the storage unit 52c. The reference measurement may be performed before the shipment of a product, or may be performed regularly.

<Sample Measurement>

The light source control unit 51*a* controls the laser light source 31 to modulate the laser oscillation wavelength within a predetermined wavelength modulation range, with a center at a modulation frequency at the peak or around the peak of the absorption spectrum of the target component.

A sample gas is introduced into the gas cell 2 by an operator or automatically, and sample measurement is then carried out.

Specifically, in the sample measurement, the logarithmic operation unit 52*a* receives an output signal from the photodetector 4, and calculates the logarithmic intensity L(t). The correlation value calculating unit 52*b* then calculates sample correlation values $S_1$ and $S_2$ of the logarithmic intensity L(t) with respect to the plurality of feature signals $F_1(t)$ and $F_2(t)$, respectively, and calculates sample correlation values $S_1'$ and $S_2'$ obtained by subtracting the reference correlation values $R_i$ from the calculated respective sample correlation values (see FIG. 5).

The concentration or partial pressure calculating unit 52*d* then solves the following simultaneous binary equations including the sample correlation values $S_1'$ and $S_2'$ calculated by the correlation value calculating unit 52*b*, the single correlation values $s_{1t}$, $s_{2t}$, $s_{1i}$, and $s_{2i}$ in the storage unit 52*c*, and the concentrations or partial pressure $C_{tar}$ and $C_{int}$ of the target component and each interference component, respectively.

$$s_{1t}C_{tar}+s_{1i}C_{int}=S_1'$$

$$s_{2t}C_{tar}+s_{2i}C_{int}=S_2'$$ [Equation 2]

As a result, through a simple and reliable operation of solving the simultaneous equations of the equation above (Equation 2), it is possible to determine the concentration or partial pressure $C_{tar}$ of the target component with the effect of interference removed.

Note that, even when there are possibly two or more interference components the effects of which are to be removed, by adding the single correlation values corresponding to the number of interference components, and solving simultaneous equations having the same number of elements as the number of types of the components, it is possible to determine the concentration or the partial pressure of the target component with the effects of the interference removed, in the same manner.

In other words, to generalize, when there are n gas species with the target component and the interference component combined in total, the following equation (Equation 3) is established, where $s_{mk}$ denotes a single correlation value of a k-th gas species with respect to an m-th feature signal, $C_k$ denotes a concentration or partial pressure of the k-th gas species, and $S_m'$ denotes a sample correlation value in the m-th feature signal $F_m(t)$.

[Equation 3]

$$s_{11}C_1 + s_{12}C_2 + s_{13}C_3 + \ldots + s_{1n}C_n = S_1'$$
$$s_{21}C_1 + s_{22}C_2 + s_{23}C_3 + \ldots + s_{2n}C_n = S_2'$$
$$s_{31}C_1 + s_{32}C_2 + s_{33}C_3 + \ldots + s_{3n}C_1 = S_3'$$
$$\vdots$$
$$s_{n1}C_1 + s_{n2}C_2 + s_{n3}C_3 + \ldots + s_{nn}C_n = S_n'$$

A concentration or a partial pressure of each gas in the target component and the interference component can be determined by solving n-dimensional simultaneous equations expressed by the equation (Equation 3).

<Pressure Sensor 7 and Structures Therearound>

Figure 6:
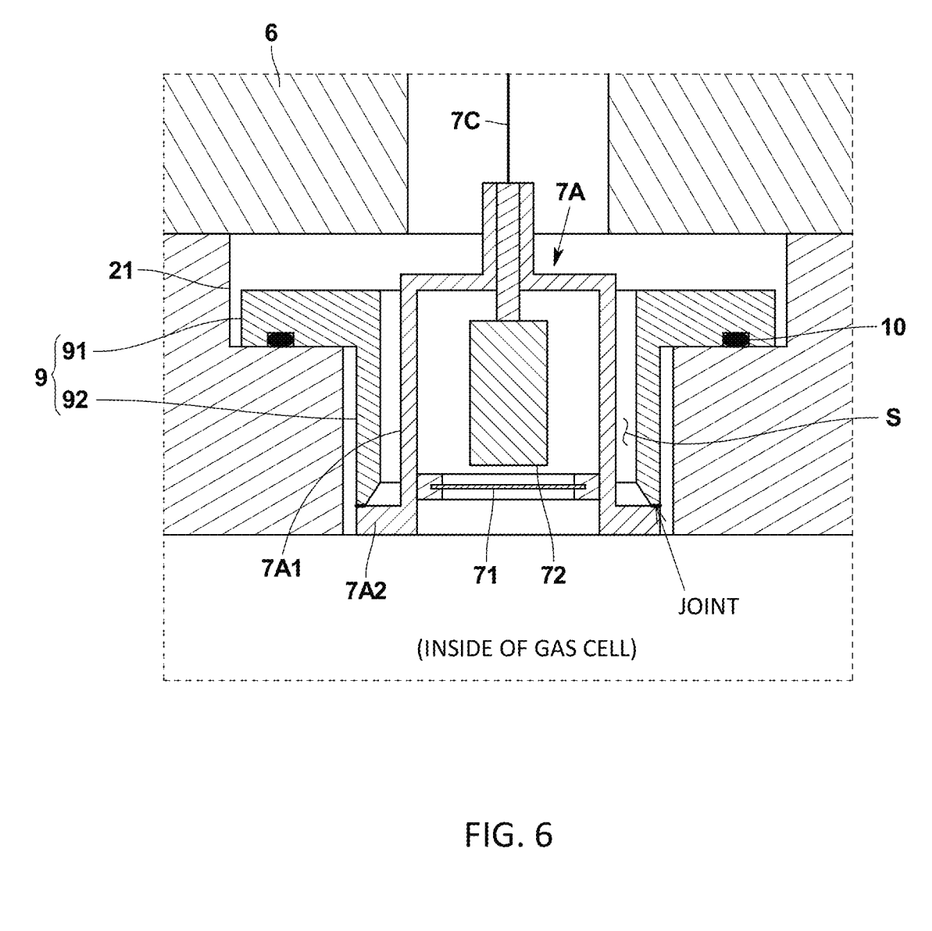
FIG. 6 is a partially enlarged cross-sectional view schematically illustrating a pressure sensor and structures around the pressure sensor according to the embodiment.

As illustrated in FIGS. 1 and 6, the gas analysis apparatus 100 according to the present embodiment includes the temperature control block 6 that controls the temperature of the gas cell 2, and the pressure sensor 7 that measures the pressure inside the gas cell 2, as described above, and the pressure sensor 7 is built into the temperature control block 6 and/or the gas cell 2.

As illustrated in FIG. 1, the temperature control block 6 is provided around the gas cell 2, and is made of a metal having high thermal conductivity, such as aluminum. The temperature control block 6 is provided around the gas cell 2 in a manner not blocking the laser light from the laser light source 31, and is provided in a manner bypassing the upstream pipe H1 and the downstream pipe H2. The temperature control block 6 is provided with a plurality of heaters 61, such as cartridge heaters, and the heaters 61 heat the temperature control block 6 to a desired temperature (for example, about 200° C.). A heat insulating member 8 is provided around the temperature control block 6. The heaters 61 may be collectively controlled by one temperature controller, or may be controlled by a plurality of respective temperature controllers that are individually provided.

The pressure sensor 7 is a capacitive pressure sensor, and includes, for example, a disk-shaped diaphragm 71 that is an example of a pressure-sensitive element that deforms with pressure, and a cylindrical fixed electrode 72, for example, that is provided in a manner facing the diaphragm 71, as illustrated in FIG. 6, and converts capacitance generated therebetween into pressure. As the pressure-sensitive element, a rectangular MEMS sensor may be used, for example.

Specifically, the pressure sensor 7 includes a sensor body 7A where the diaphragm 71 and the fixed electrode 72 are provided, and a circuit board 7B that converts capacitance between the diaphragm 71 and the fixed electrode 72 into pressure. In the present embodiment, the sensor body 7A and the circuit board 7B are connected by a signal cable 7C, such as a shielded cable. The sensor body 7A according to the present embodiment has a substantially cylindrical shape.

The pressure sensor 7 is built into the temperature control block 6 and the gas cell 2. Specifically, the sensor body 7A of the pressure sensor 7 is built into the temperature control block 6 and the forming walls 2*a* of the gas cell 2. An attaching portion 21 for fixing the sensor body 7A is formed on the temperature control block 6 and the forming walls 2*a* of the gas cell 2, in a manner communicating with the gas cell 2.

The sensor body 7A is fixed, by an annular flange member 9, to an attaching portion 21 formed on a forming wall 2*a* of the gas cell 2. A gap S serving as a heat buffer layer is formed between the outer peripheral surface of the sensor body 7A and the flange member 9 across the entire circumferential direction.

In the present embodiment, a collar 7A2 is provided across the entire circumference of the outer peripheral surface of a cylindrical case 7A1 of the sensor body 7A. The flange member 9 has an annular fixed portion 91 that is fixed to the attaching portion 21 of the gas cell 2, and a cylindrical support 92 that extends from an inner side of an opening of the fixed portion 91 and that is connected to the collar 7A2 of the sensor body 7A. Note that a seal member 10 is provided between the attaching portion 21 and the fixed portion 91 to ensure airtightness. In addition, the seal member 10 may be provided between the inner peripheral surface of the attaching portion 21, for example, and the outer peripheral surface of the support 92, for example, or may be provided at any position as long as airtightness of the gas cell 2 can be ensured.

A tip end of the support 92 is joined to an axial rear end surface (on an axially outer surface) of the collar 7A2 by welding, such as laser welding. The tip portion of the support 92 may also be connected to the collar 7A2 with screws. The support 92 has a cylindrical shape having an inner diameter larger than the outer diameter of the cylindrical case 7A1 of the sensor body 7A, and the gap S serving as a heat buffer layer is formed between the support 92 and the outer peripheral surface of the cylindrical case 7A1 across the entire circumferential direction, with the support 92 welded to the axial rear end surface of the collar 7A2. The gap S may be filled with a member to suppress unevenness in the heat transferred to the sensor body 7A.

With the above configuration, the temperature of the sensor body 7A is controlled by the temperature control block 6 via the flange member 9. Specifically, heat is transferred from the temperature control block 6 to the forming walls 2a and 2b of the gas cell 2, and the temperature of the gas cell 2 is controlled thereby. In addition, the heat is transferred from the forming walls 2a of the gas cell 2, the temperature of which is controlled, to the flange member 9, and the heat is transferred from the flange member 9 to the sensor body 7A via the gap S, so that the temperature of the sensor body 7A (specifically, the diaphragm 71) is controlled thereby. In this manner, temperature unevenness of the diaphragm 71 is reduced. In the manner described above, the temperature control block 6 that controls the temperature of the gas cell 2 is also used in controlling the temperature of the sensor body 7A.

Furthermore, in the pressure sensor 7 according to the present embodiment, the sensor body 7A and the circuit board 7B are connected via the signal cable 7C, and the circuit board 7B is provided at a portion where the temperature is low, e.g., room temperature, outside the heat insulating member 8 that is provided around the temperature control block 6.

Advantageous Effects Achieved by Present Embodiment

In the gas analysis apparatus 100 according to the present embodiment configured as described above, because the pressure sensor 7 is built into the temperature control block 6 and/or the gas cell 2, the temperature of the pressure sensor 7 can be controlled using the temperature control block 6. As a result, it is not necessary to provide a temperature control mechanism for controlling the temperature of the pressure sensor 7, separately, so that the size of the gas analysis apparatus 100 can be reduced. By controlling the temperature of the pressure sensor 7, the accuracy of the pressure measurement can be improved, and the concentration of a gas component can be measured highly accurately. Furthermore, by installing the pressure sensor 7 in a manner built into the gas cell 2, the distance between the optical path (concentration measurement point) and a pressure detection position, the pressure to be used for correction, is reduced as much as possible, and a deviation in their response time is also reduced. Therefore, the accuracy of concentration reading can be improved.

In addition, in the present embodiment, because the temperature of the sensor body 7A is controlled by the temperature control block 6 indirectly via the flange member 9, a temperature change caused by the effect of disturbance propagates slowly. Therefore, it is possible to make the sensor body 7A less susceptible to the effect of disturbance. In addition, it is possible to suppress the thermal distribution across the sensor body 7A. As a result, a pressure can be measured accurately.

Furthermore, in the present embodiment, because the gap S serving as the heat buffer layer is formed between the outer peripheral surface of the sensor body 7A and the flange member 9, the temperature of the sensor body 7A can be controlled while suppressing the thermal distribution of the sensor body 7A. Therefore, the pressure can be measured accurately.

In addition, because the circuit board 7B of the pressure sensor 7 is provided outside the temperature control block 6 via the signal cable 7C, the circuit board 7B can be kept away from the heat source (the temperature control block 6 in this example), so that it is possible to suppress the thermal effect on the circuit board 7B.

Other Embodiments

Figure 7:
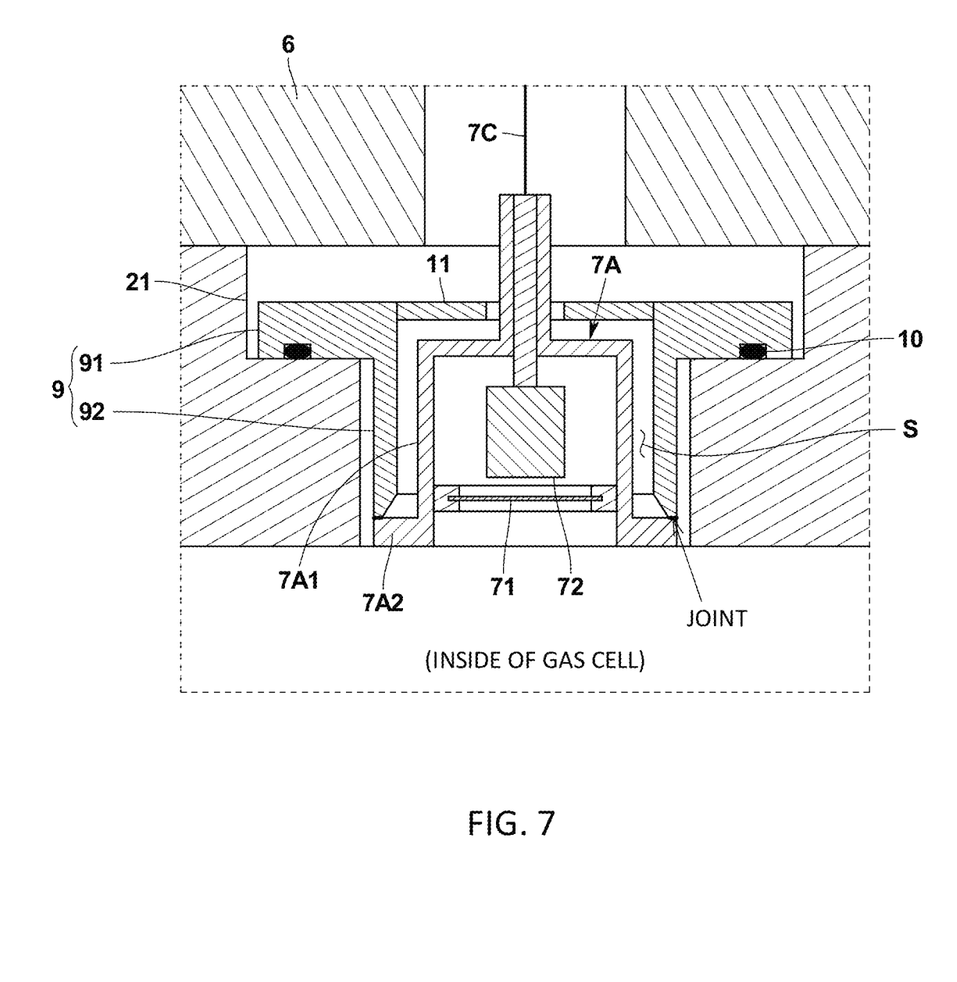
FIG. 7 is a partially enlarged cross-sectional view schematically illustrating a pressure sensor and structures around the pressure sensor according to a modified embodiment.

For example, in addition to the configuration of the above embodiment, the rear end surface of the sensor body 7A on the side opposite to the sensor surface (tip end surface) may be covered with a cover 11 with a gap S therebetween, as illustrated in FIG. 7, in addition to covering the outer peripheral surface of the sensor body 7A with the flange member 9. In addition, a member other than the flange member 9, e.g., the gas cell 2 or the temperature control block 6, may cover the rear end surface of the sensor body 7A with the gap S therebetween.

Figure 8:
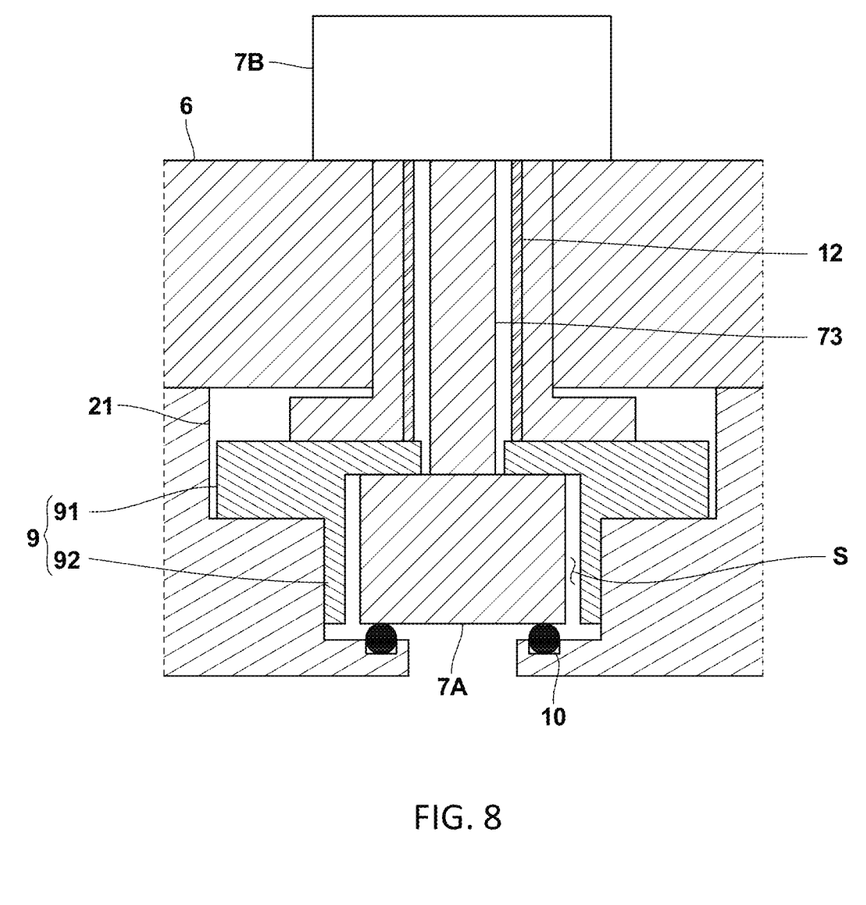
FIG. 8 is a partially enlarged cross-sectional view schematically illustrating a pressure sensor and structures around the pressure sensor according to a modified embodiment.

In addition, as illustrated in FIG. 8, the sensor body 7A and the circuit board 7B may be connected to each other by a metal stem 73 and integrated with each other. In such a configuration, the sensor body 7A and the circuit board 7B are connected by the metal stem 73 that is connected to the fixed electrode 72, and the circuit board 7B is provided outside the heat insulating member 8 provided around the temperature control block 6. Furthermore, around the metal stem 73, an insulating member 12 such as PTFE may be provided. In FIG. 8, the seal member 10 is provided between the sensor body 7A and the attaching portion 21 to ensure airtightness, but it is also possible for the seal member 10 to be provided between the flange member 9 and the attaching portion 21.

Furthermore, the temperatures of the plurality of heaters 61 provided in the temperature control block 6 may be controlled individually. With this configuration, it is possible to control the temperature appropriately, by dividing the areas of the temperature control block 6 into temperature control areas for the pressure sensor 7 and for the gas cell 2, for example.

The pressure sensor according to the above embodiment is not limited to the capacitive pressure sensor, and may be, for example, a Pirani vacuum gauge, a cold cathode ionization vacuum gauge, or a hot cathode ionization vacuum gauge.

Furthermore, the logarithmic operation unit 52a according to the embodiment described above performs a logarithmic operation on the light intensity signal of the photodetector 4, but may also calculate the logarithm of a ratio between the intensity of the sample light and the intensity of a modulated light that is the reference light (what is called absorbance) using the light intensity signal of the photodetector 4. At this time, the logarithmic operation unit 52a may calculate the absorbance by calculating the logarithm of the intensity of the sample light, calculating the logarithm of the intensity of the modulated light, and then subtracting the latter from the former, or may calculate the absorbance by obtaining a ratio between the intensity of the sample light and the intensity of the modulated light, and then taking the logarithm thereof.

In addition, the correlation value calculating unit 52b according to the embodiment described above calculates a correlation value for the intensity-related signal with respect to each of the feature signals, but may calculate an inner product of the intensity-related signal and each of the feature signals.

In the embodiment described above, the storage unit 52c stores therein the single correlation value corrected using the reference correlation value. Alternatively, the storage unit 52c may store therein an uncorrected single correlation value, and the concentration or partial pressure calculating unit 52d may obtain the corrected single correlation value by subtracting the reference correlation value from the uncorrected single correlation value and converting the result to a per-unit concentration.

The plurality of feature signals is not limited to the above embodiment, and may be any functions that are different from one another. In addition, for example, it is also possible to use a function indicating a waveform (sample spectrum) of light intensity or a logarithmic intensity obtained by sending a span gas having a known concentration or partial pressure, as a feature signal. To measure the concentration of one target component, it is sufficient if there is at least one feature signal.

Furthermore, it is also possible to use a least squares method to determine the concentration or the partial pressure of each component, by formulating, using the feature signals of the number of types of which is more than n, simultaneous equations including elements greater in number than the number of gas species, and obtaining single correlation values and sample correlation values the numbers of which are greater than the number of gas species. In this manner, it is possible to determine the concentration or the partial pressure with the error reduced, even with respect to a measurement noise.

The signal processing unit according to the embodiment performs the functions of the correlation value calculating unit that calculates a correlation value that is dependent on the concentration or the partial pressure of the target component, using an intensity-related signal related to the intensity of the sample light and a feature signal, from which a predetermined correlation value is obtained with respect to the intensity-related signal, and the concentration or partial pressure calculating unit that calculates the concentration or the partial pressure of the target component using the correlation value obtained by the correlation value calculating unit. However, other calculation methods may also be used.

Furthermore, regardless of the semiconductor laser, the light source may be another type of laser, or any light source may be used as long as the light source is a single-wavelength light source having a line width sufficient to ensure the measurement accuracy, and that can perform wavelength modulation. Alternatively, the intensity of the light source may be modulated. Furthermore, as the light source, a light source emitting light at various wavelengths, such as a light source that emits infrared light or a light source that emits ultraviolet light may be used. Specifically, the light source is not limited to a laser light source that emits laser light, and various types of light sources may be used as long as the light source emits light, such as a thermal light source, an LED light source, a deuterium lamp, and a xenon lamp.

The method for calculating a concentration or a partial pressure of the target component in the gas analysis apparatus is not limited to the above embodiment, and various methods such as direct absorption method or wavelength modulation spectroscopy (WMS method) may be used.

In addition, various modifications and combinations of the embodiments may be made within the scope not deviating from the gist of the present invention.

REFERENCE SIGNS LIST

100 gas analysis apparatus
2 gas cell
3 light irradiating unit
4 photodetector
5 signal processing apparatus
6 temperature control block
61 heater
7 pressure sensor
7A sensor body
71 diaphragm (pressure-sensitive element)
7A2 collar
7B circuit board
7C signal cable
8 heat insulating member
9 flange member
91 fixed portion
92 support
S heat buffer layer

What is claimed is:

1. A gas analysis apparatus comprising:
    a gas cell into which a gas is introduced;
    a light irradiator configured to emit light into the gas cell;
    a photodetector configured to detect the light having passed through the gas cell;
    a temperature control block provided around the gas cell and configured to control a temperature of the gas cell;
    a pressure sensor configured to measure a pressure inside the gas cell and includes a sensor body that includes a pressure-sensitive element; and
    a flange member fixed to an attaching portion that is formed on the temperature control block and the forming wall of the gas cell, in a manner communicating with the gas cell,
    wherein the sensor body is fixed, by the flange member, to the attaching portion on the forming wall of the gas cell, and has a temperature controlled by the temperature control block via the flange member.

2. The gas analysis apparatus according to claim 1, wherein the pressure sensor is a capacitive pressure sensor.

3. The gas analysis apparatus according to claim 1, wherein a gap is formed between an outer peripheral surface of the sensor body and the flange member.

4. The gas analysis apparatus according to claim 3, further comprising a cover that covers a rear end surface of the sensor body, with a gap between the cover and the rear end surface, the rear end surface being on a side opposite to a sensor surface of the sensor body.

5. The gas analysis apparatus according to claim 1, wherein
a collar is provided on an outer peripheral surface of the sensor body, and
the flange member includes a fixed portion that is fixed to the gas cell, and a support that extends from the fixed portion and that is connected to the collar of the sensor body.

6. The gas analysis apparatus according to claim 1, wherein
the pressure sensor includes a circuit board configured to process a detection signal, and
the circuit board is provided outside the temperature control block via a signal cable.

7. The gas analysis apparatus according to claim 1, wherein
the temperature control block includes a plurality of heaters, and
temperatures of the plurality of heaters are controlled individually.

8. A gas analysis method, comprising:
performing a gas analysis using a gas analysis apparatus, wherein the gas analysis apparatus includes:
a gas cell into which a gas is introduced,
a light irradiator configured to emit light into the gas cell,
a photodetector configured to detect the light having passed through the gas cell,
a temperature control block provided around the gas cell and configured to control a temperature of the gas cell, and
a pressure sensor configured to measure a pressure inside the gas cell and includes a sensor body that includes a pressure-sensitive element,
wherein the sensor body is fixed, by a flange member, to the attaching portion on a forming wall of the gas cell, and has a temperature controlled by the temperature control block via the flange member.

* * * * *